(12) United States Patent
Salin et al.

(10) Patent No.: US 11,033,762 B2
(45) Date of Patent: Jun. 15, 2021

(54) APPARATUS AND METHOD FOR MONITORING BREATHING AIR

(71) Applicant: Insta ILS Oy, Tampere (FI)

(72) Inventors: Jukka Salin, Tampere (FI); Ville Tipuri, Tampere (FI); Juha Pitkänen, Tampere (FI); Sami Hakola, Tampere (FI); Ville Kettula, Tampere (FI); Ville Soininen, Tampere (FI); Jarmo Skyttä, Riihimäki (FI)

(73) Assignee: Insta ILS Oy, Tampere (FI)

( * ) Notice: Subject to any disclaimer, the term of this patent is extended or adjusted under 35 U.S.C. 154(b) by 278 days.

(21) Appl. No.: 15/685,184

(22) Filed: Aug. 24, 2017

(65) Prior Publication Data

US 2018/0126194 A1 May 10, 2018

(30) Foreign Application Priority Data

Aug. 24, 2016 (EP) .................................. 16397527

(51) Int. Cl.
*A62B 18/08* (2006.01)
*A61B 5/00* (2006.01)
(Continued)

(52) U.S. Cl.
CPC ............ *A62B 18/08* (2013.01); *A61B 5/0826* (2013.01); *A61B 5/0833* (2013.01);
(Continued)

(58) Field of Classification Search
None
See application file for complete search history.

(56) References Cited

U.S. PATENT DOCUMENTS 3,572,331 A 3/1971 Kissen
3,587,438 A * 6/1971 Foster .................... B64D 13/04
454/70
(Continued)

FOREIGN PATENT DOCUMENTS

WO 2012114145 A1 8/2012
WO 2012116764 A1 9/2012

OTHER PUBLICATIONS

Ahrens et al. "Essentials of Oxygenation: Implication for Clinical Practice", Jones and Bartlett Publishers, Jan. 15, 1993, ISBN-10: 0867203323, ISBN-13: 978-0867203325, pp. 20-31.
Extended European Search Report, Application No. 16397527.9, dated Mar. 1, 2017, 8 pages.

*Primary Examiner* — Matthew Kremer
*Assistant Examiner* — Samuel C Kim
(74) *Attorney, Agent, or Firm* — Ziegler IP Law Group, LLC

(57) ABSTRACT

A method for monitoring breathing air of a person breathing via a face mask (8). In the method pressure of inhaled air and partial pressure of oxygen before oxygen enters in the face mask (8) are measured. A partial pressure of oxygen in lungs of the person is estimated on the basis of the measured pressure of inhaled air and the measured partial pressure of oxygen. Also at least one physical characteristics of lungs is taken into account. The estimated partial pressure of oxygen in lungs is compared with a threshold. An indication of impending hypoxia is provided to the person, if the comparison indicates that the estimated partial pressure of oxygen in lungs is at a level lower than the threshold. The present disclosure also relates to an apparatus (6) for implementing the method.

16 Claims, 1 Drawing Sheet

(51) Int. Cl.
  *A61B 5/08*   (2006.01)
  *A61B 5/083*  (2006.01)
  *A62B 7/08*   (2006.01)
  *A62B 7/14*   (2006.01)
  *A62B 9/00*   (2006.01)
  *A62B 18/02*  (2006.01)
  *B64D 13/06*  (2006.01)
  *A61B 5/145*  (2006.01)

(52) U.S. Cl.
  CPC .......... *A61B 5/6803* (2013.01); *A61B 5/7275* (2013.01); *A61B 5/742* (2013.01); *A61B 5/7405* (2013.01); *A61B 5/746* (2013.01); *A61B 5/7455* (2013.01); *A62B 7/08* (2013.01); *A62B 7/14* (2013.01); *A62B 9/006* (2013.01); *A62B 18/02* (2013.01); *A61B 5/14542* (2013.01); *A61B 2503/22* (2013.01); *A61B 2560/0214* (2013.01); *A61B 2560/0257* (2013.01); *A61B 2562/0247* (2013.01); *A61B 2562/0271* (2013.01); *B64D 2013/0677* (2013.01)

(56) References Cited

U.S. PATENT DOCUMENTS

| 4,651,728 | A | 3/1987 | Gupta et al. | |
|---|---|---|---|---|
| 7,040,319 | B1 | 5/2006 | Kelly et al. | |
| 2004/0206352 | A1* | 10/2004 | Conroy, Jr. | A61B 5/14551 128/204.23 |
| 2010/0012116 | A1* | 1/2010 | Rittner | A62B 7/08 128/202.26 |
| 2010/0057046 | A1* | 3/2010 | Stevens | A61B 5/02055 604/507 |
| 2012/0055815 | A1* | 3/2012 | Truex | A62B 9/006 206/205 |
| 2013/0312745 | A1* | 11/2013 | Kshirsagar | B64D 11/00 128/202.26 |
| 2013/0327330 | A1* | 12/2013 | Fromage | A62B 7/14 128/204.22 |
| 2015/0047638 | A1* | 2/2015 | Robey | A62B 7/02 128/204.22 |
| 2015/0196245 | A1 | 7/2015 | Peake | |

* cited by examiner

APPARATUS AND METHOD FOR MONITORING BREATHING AIR

TECHNICAL FIELD

The present invention relates to a method for monitoring breathing air of a person breathing via a face mask. The invention also relates to an apparatus for monitoring breathing air of a person breathing via a face mask.

BACKGROUND

Hypoxia is known as a condition in which a human body does not have sufficient oxygen in cardiovascular system. In other words, the human body is deprived of adequate oxygen supply. Hypoxia may affect to the capacity of the human body, may slow down activity and reaction ability of the human body, may cause unconsciousness, and may even be fatal. Hypoxia is insidious because it decreases the level of human consciousness. It is difficult for humans to even notice the symptoms of hypoxia. For example, if a pilot of an airplane begins to suffer hypoxia, he/she may not be able to control the airplane accurately and fast enough although pilot may believe his/her performance is on a normal level. Therefore, it may be necessary to control concentration of oxygen in the blood circulation of the pilot and warn the pilot before hypoxia. Another cause for hypoxia may be that the breath air contains toxic compound(s) such as carbon monoxide.

U.S. Pat. No. 3,572,331 discloses an impending hypoxia detection and warning system for aircraft personnel. The system monitors each breath of a person by a dry electrolyte oxygen partial pressure ($pO_2$) sensing cell. An electronic circuit responsive to the oxygen sensor counts breaths exhibiting maximal partial pressure of oxygen values below an electronically preset equivalent partial pressure of oxygen, and after a predetermined number of successive counts an alarm circuit is energized until the oxygen partial pressure rises above the predetermined level. The system measures oxygen partial pressure in a face mask of the person and activates the alarm when the oxygen partial pressure in the face mask remains below the predetermined level for certain number of breaths. This kind of system has some disadvantages. For example, the sensor monitors the oxygen partial pressure in the face mask. This may not fully correspond the actual oxygen partial pressure in the person's blood circulation, wherein there may be a delay before the system notices that the oxygen partial pressure has dropped below the predetermined level. This delay may cause that the person is warned too late and may suffer hypoxia before the alarm is activated.

Another method to measure partial pressure of a human is known as Alveolar gas equation, disclosed, for example, by Ahrens & Rutherford, "Essentials of Oxygenation", 1993, pages. 20-32.

SUMMARY

An aim of the present invention is to provide an improved apparatus and method for breath air monitoring, which may enable to activate an alarm of impeding hypoxia before a pilot is already suffering hypoxia. The invention is based on the idea that pressure of inhaled air and oxygen partial pressure are measured, the measurement results are used to estimate oxygen partial pressure in the lungs of the pilot, and if certain predetermined conditions are fulfilled, the pilot is warned by at least one haptic signal. Estimating the oxygen partial pressure in the lungs may indicate impending hypoxia earlier than in a situation in which only oxygen partial pressure in a face mask is measured.

According to a first aspect, there is provided a method for monitoring breathing air of a person breathing via a face mask, the method comprising:
   measuring pressure of inhaled air;
   measuring partial pressure of oxygen before oxygen enters the face mask;
   estimating a partial pressure of oxygen in lungs of the person on the basis of the measured pressure of inhaled air and the measured partial pressure of oxygen;
   comparing the estimated partial pressure of oxygen in lungs with a threshold and taking at least one physical characteristic of lungs into account; and
   providing an indication of impending hypoxia to the person, if the comparison indicates that the estimated partial pressure of oxygen in lungs is at a level lower than the threshold.

According to a second aspect, there is provided an apparatus for monitoring breath of a person breathing via a face mask, the apparatus comprising:
   a pressure sensor for measuring pressure of inhaled air;
   a partial pressure sensor for measuring partial pressure of oxygen before oxygen enters the face mask;
   means for estimating a partial pressure of oxygen in lungs of the person on the basis of the measured pressure of inhaled air and the measured partial pressure of oxygen;
   means for comparing the estimated partial pressure of oxygen in lungs with a threshold and taking at least one physical characteristic of lungs into account; and
   means for providing an indication of impending hypoxia to the person when the comparison indicates that the estimated partial pressure of oxygen in lungs is at a level lower than the threshold.

Some advantages may be obtained by the invention. For example, activating an alarm before pilot performance degrades may give more time to react and avoid loss of consciousness of the pilot. The usage of the system does not require any extra activities by the pilot. The monitoring apparatus may be automatically calibrated during operation time. Hence, no separate calibration operations may be needed.

BRIEF DESCRIPTION OF THE DRAWINGS

In the following the invention will be described in more detail with reference to the appended drawings, in which.

DETAILED DESCRIPTION

Figure 1:
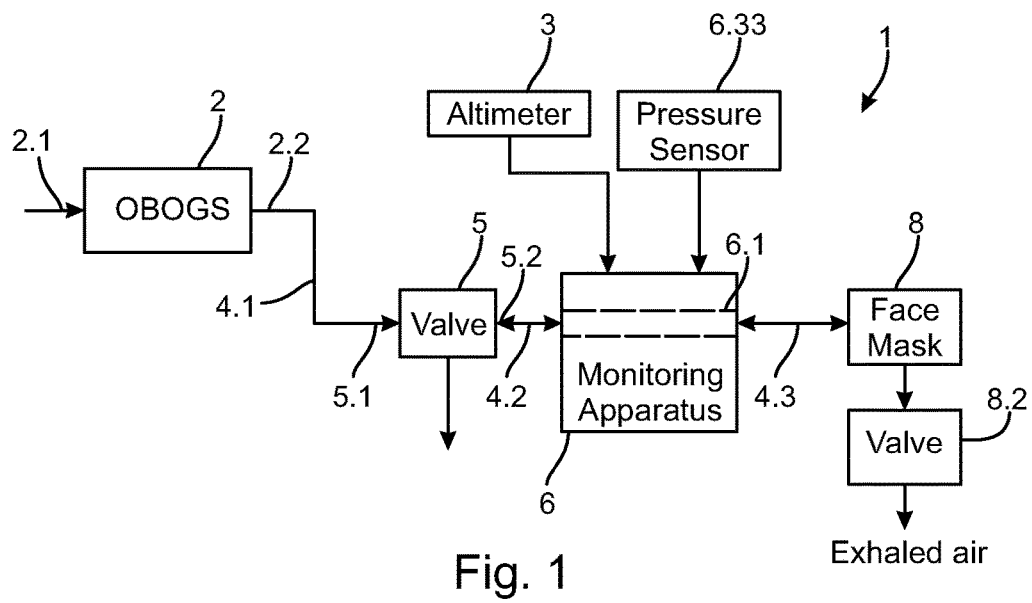
FIG. 1 illustrates as a block diagram some elements of a breath air system for a pilot, in accordance with an embodiment.

FIG. 1 illustrates a breath air system 1 for a pilot, in accordance with an embodiment. The system 1 comprises an onboard oxygen generation system 2 which generates a mixture of gases for the pilot. The onboard oxygen generation system 2 may have one or more inlets 2.1 for receiving gases to be used in breath air generation. The onboard oxygen generation system 2 may use bleed air from an engine, an ambient air and/or other sources of gaseous compounds. A mixture of gaseous compounds generated by the onboard oxygen generation system 2 are provided via an outlet 2.2. The mixture comprises oxygen and may also comprise other gases to provide breath air for the pilot. The other gases may include, among other things, nitrogen. However, instead of or in addition to the onboard oxygen generation system 2 an oxygen container may be used to provide oxygen to the pilot. The system 1 may also comprise a pressure sensor 6.33 for measuring pressure of the cabin of the airplane and possibly an altimeter 3 for measuring the altitude the airplane is flying. The pressure and/or altitude information may be used, for example, to warn the pilot that the pressure is too low and/or the plane is flying at too high altitude, for example if the cabin is unpressurised. If the cabin pressure is too low, it may happen that even 100% oxygen concentration is not sufficient for assuring that the pilot has enough oxygen in the lungs. As an example, the amount of nitrogen may be reduced at higher altitudes and/or smaller cabin pressures. The output fluid from the onboard oxygen generation system 2 is conducted from the outlet 2.2 via a first conduit 4.1 to an inlet 5.1 of a valve 5. The valve 5 may operate so that when the pilot inhales, the valve passes output fluid from the onboard oxygen generation system 2 to a first outlet 5.2 of the valve 5. A second conduit 4.2 may be coupled between the first outlet 5.2 of the valve 5 and a monitoring apparatus 6, or the first outlet 5.2 may be directly coupled with the monitoring apparatus 6. The monitoring apparatus 6 measures, among other things, partial pressure of oxygen in the output fluid i.e. in the fluid of gaseous compounds from the onboard oxygen generation system 2. The monitoring apparatus 6 has a fluid passage 6.1 which enables flow of the fluid through the monitoring apparatus 6. A third conduit 4.3 may be used to further conduct the output fluid from the fluid passage 6.1 of the monitoring apparatus 6 to a face mask 8 of the pilot, for example to a breathing hose of the face mask 8. Thus, the output fluid from the onboard oxygen generation system 2 is provided to the face mask 8 so that the pilot may use the output fluid as breathable air. At an exhalation phase of the pilot exhaled air may be led outside the face mask 8 via an exhaled gas valve 8.2.

Figure 2:
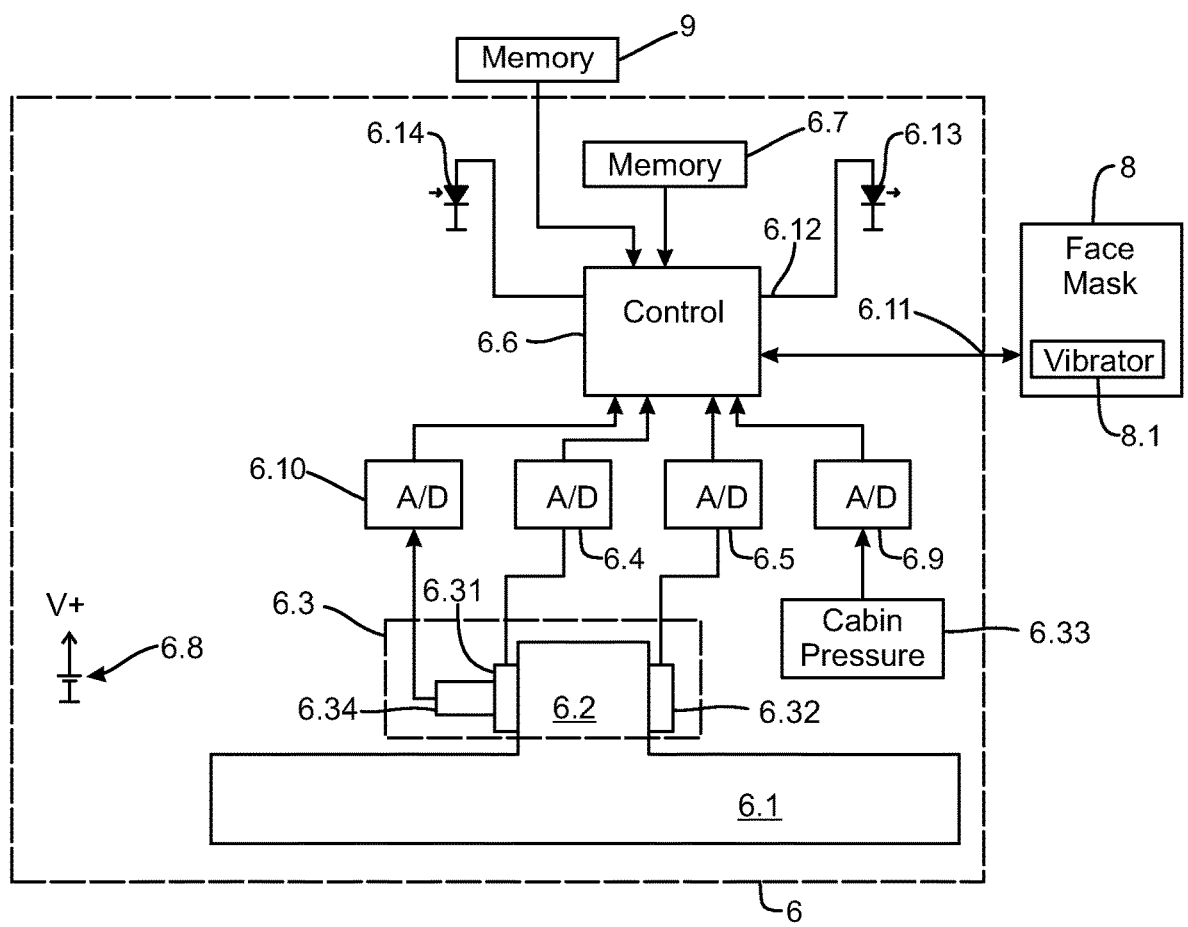
FIG. 2 illustrates as a block diagram some elements of a monitoring apparatus, in accordance with an embodiment.

FIG. 2 illustrates some elements of the monitoring apparatus 6 as a block diagram, in accordance with an embodiment. The monitoring apparatus 6 comprises a measurement chamber 6.2 which may comprise a sensor assembly 6.3. The sensor assembly 6.3 is provided with one or more sensors for measuring different agents/substances present in the measurement chamber 6.2. In accordance with an embodiment the sensor assembly 6.3 comprises an oxygen partial pressure sensor 6.31 and a pressure sensor 6.32. The measurement chamber 6.2 has a flow connection with a fluid passage 6.1 of the monitoring apparatus 6. Hence, flow of gaseous substances may also enter the measurement chamber 6.2, wherein sensor(s) 6.31, 6.32 of the sensor assembly 6.3 are able to provide measurement signals indicative of the amount of the quantity to be measured. For example, the oxygen partial pressure sensor 6.31 measures partial pressure of oxygen and the pressure sensor 6.32 measures pressure of breath air inside the fluid passage 6.1. Measurement signals from the oxygen partial pressure sensor 6.31 are coupled to a first analog-to-digital converter 6.4 (A/D), and measurement signals from the pressure sensor 6.32 are coupled to a second analog-to-digital converter 6.5. The first analog-to-digital converter 6.4 converts analogue measurement values of the measurement signal of the oxygen partial pressure sensor 6.31 into digital samples representing the measurement signal. Correspondingly, the second analog-to-digital converter 6.5 converts analogue measurement values of the measurement signal of the pressure sensor 6.32 into digital samples representing the measurement signal. Digital samples from the first analog-to-digital converter 6.4 and digital samples from the second analog-to-digital converter 6.5 are provided to a processor 6.6. The processor 6.6 may be used to perform signal processing operations and algorithms to estimate whether the pilot is in a risk of an impending hypoxia. Computer codes for operations of the processor 6.6 including computer code for the signal processing operations and algorithms may be stored into a memory 6.7 of the monitoring apparatus 6. The memory 6.7 and/or an external memory 9 may be used to store digital samples, parameters and/or other information during the operation of the monitoring apparatus 6. The memory 6.7 and/or the external memory 9 may also be able to maintain some or all of the stored digital samples, parameters and/or other information when the monitoring apparatus 6 is not in operation. The storage which is used for storing information may be arranged as a so-called ring-buffered file system, wherein the storage may have a fixed length and if it becomes full of data, oldest data is written over by newest data.

The sensor assembly 6.3 may further comprise a cabin pressure sensor 6.33 for measuring pressure in the cabin of the airplane, and/or a temperature sensor 6.34 for measuring temperature of the oxygen partial pressure sensor 6.31 and/or the pressure sensor 6.32. The monitoring apparatus 6 may also comprise other sensors and/or components not shown in FIG. 2. For example, the sensor assembly 6.3 may have a voltage measurement sensor to measure the voltage level of a battery 6.8 of the apparatus. A third analog-to-digital converter 6.9 converts analogue measurement values of the cabin pressure sensor 6.33 into digital samples, and a fourth analog-to-digital converter 6.10 converts analogue measurement values of the temperature sensor 6.34 into digital samples.

It should be noted that the monitoring apparatus 6 need not have a separate analogue-to-digital converter for each measurement signal to be converted into digital samples but operation of one analogue-to-digital converter may be adapted to convert measurement signals from more than one sensor into digital samples. Moreover, some of the elements of the monitoring apparatus may be included in the processor 6.6. As an example, the processor 6.6 may comprise one or more analogue-to-digital converters, memory, etc.

The face mask 8 may comprise a haptic signal generation element 8.1 so that the face mask may vibrate when the monitoring apparatus 6 activates an alarm.

The measurement results of the oxygen partial pressure and the pressure of breath air may be used by the processor 6.6 to estimate oxygen partial pressure inside lungs of the pilot. In the estimation some assumptions may be used e.g. to make the estimation easier. For example, it may be assumed that the pilot is a normal, healthy person and that the environment within the cabin are controlled and/or monitored with the apparatus. Furthermore, it may be assumed that the breath air system 1 utilizes rich in oxygen. Therefore, these parameters may be assumed to be constant.

The estimated oxygen partial pressure inside lungs of the pilot may be compared with a threshold and if the comparison results indicate that the oxygen partial pressure inside lungs of the pilot is too low, the processor 6.6 may activate a warning or an alarm. When performing the comparison, also one or more physiological characteristics of lungs may be taken into account. For example, partial pressure of water vapor in lungs may be one physiological factor of the lungs which may be taken into account when deciding whether to activate the warning or alarm or not. The activation of the warning/alarm may include generating an haptic indication and possibly another indication in another form, such as a visual alarm indication and/or a sound alarm. In accordance with an embodiment, a warning is generated first and if the situation becomes worse or if the apparatus determines that the pilot has not initiated necessary steps to avoid hypoxia, an alarm may be generated.

In accordance with an embodiment, the monitoring apparatus 6 comprises an output 6.11 which may be coupled to the vibrating element 8.1 in the face mask 8. Hence, when the monitoring apparatus 6 activates an alarm, the state of the output 6.11 is changed so that the vibrating element 8.1 begins to vibrate. If also a visual alarm indication is generated, the processor 6.6 may change the state of a light source control output 6.12 coupled to a light source 6.13. Hence, the light source 6.13, which may comprise, for example, one or more light emitting diodes (LED), begins to illuminate. In accordance with an embodiment, the monitoring apparatus 6 may be adapted to adjust the brightness of the light source(s) 6.13 on a basis of a brightness indication provided by a brightness indicator 6.14 such as a photo diode.

The processor 6.6 may start logging of measurement data into the memory 6.7, 9 at shorter intervals when an alarm is activated and may continue the accelerated logging until the alarm is deactivated. Logging interval when an alarm is activated as well as when no alarms are activated may be fixed or adjustable. Also different data may have different logging intervals. Stored data may later be retrieved from the monitoring apparatus 2 for analyses and/or other purposes.

In accordance with an embodiment, the monitoring apparatus 6 may also be used to monitor concentration of other compounds than oxygen in the air supplied to the pilot. As an example, the sensor assembly 6.3 may have a sensor for monitoring carbon monoxide (CO), a sensor for monitoring carbon dioxide ($CO_2$), etc. Excessive amounts of carbon monoxide in the breath air may be, for example, due to misbehaviour of the onboard oxygen generation system 2 and/or contaminated ambient air.

In accordance with an embodiment, the monitoring apparatus 6 may generate different alarm indications for different situations. For example, when the pilot has a risk of hypoxia, the monitoring apparatus 6 may control the vibrating element 8.1 so that it vibrates according to a first vibration pattern, when the level of carbon monoxide (CO) in the breath air exceeds a CO-level threshold, the monitoring apparatus 6 may control the vibrating element 8.1 so that it vibrates according to a second vibration pattern, when the level of carbon dioxide ($CO_2$) in the breath air exceeds a $CO_2$-level threshold, the monitoring apparatus 6 may control the vibrating element 8.1 so that it vibrates according to a third vibration pattern, when the pressure level in the cabin falls below a pressure-level threshold, the monitoring apparatus 6 may control the vibrating element 8.1 so that it vibrates according to a fourth vibration pattern etc. Similar behaviour may be provided to the visual and/or audible alarm indication(s).

The monitoring apparatus 6 may also have a self-test procedure which may be initiated by the pilot before or during flight.

The monitoring apparatus 6 may be coupled to the pilot's breathing hose assembly. In accordance with an embodiment, the monitoring apparatus 6 may be automatically switched on when connected to the breathing hose assembly and switched off when disconnected from the breathing hose assembly. This may be implemented e.g. so that when wires of the vibrating element 6.1 attached with the breathing hose assembly is coupled with the output 6.11 of the apparatus, this is detected and the monitoring apparatus 6 is switched on. Another example implementation may use a switch arranged in the breathing hose assembly wherein attaching the output 6.11 of the apparatus with the breathing hose assembly may close the switch and turn the monitoring apparatus 6 on. In accordance with another embodiment, the monitoring apparatus 6 may be manually switched on and off e.g. by the pilot.

In accordance with an embodiment, the monitoring apparatus 6 may also comprise leakage detection operations. Leakage detection can be detected, for example, by measuring pressure of the breathing hose. If the measurement results indicate that the pressure remains substantially the same, i.e. changes are not detected, it may indicate that there is leakage in the hosing between the equipment and pilot's face mask 8.

In accordance with yet another embodiment, the monitoring apparatus 6 may also measure respiration frequency. It may be performed e.g. so that the monitoring apparatus 6 measures pressure of the breathing hose. When the pilot breaths there should be changes in the pressure as a consequence of exhalation and inhalation of the pilot. The pressure changes can be analyzed to determine regularities in the pressure changes from which a respiration frequency can be determined. Hence, if it is determined that the respiration frequency is outside of a predetermined range, an alarm may be rised to warn the pilot.

Electricity may be supplied by the battery 6.8 and/or by an external voltage supply (not shown).

The monitoring apparatus 6 may be able to communicate with a control system of the airplane wirelessly and/or using wired communication means.

The above description used an airplane as an example of an application where the monitoring apparatus 6 may be used but it may also be possible to use the monitoring apparatus 6 in other applications as well, where concentration of gaseous compound(s) and risk for hypoxia may occur or hazardous gas components needs to monitored.

Parameters, alarm/warning conditions etc. may be user-dependent wherein the monitoring apparatus 6 may take user properties in condition when examining measurement data. In other words, different persons may have different physical properties which may affect to the conditions when the person has a risk of hypoxia. Therefore, the user may be identified by the monitoring apparatus 6 and adjust/select parameters for that particular user. The identification may be based on an RFID (radio frequency identification) tag, manual selection or another appropriate method.

As an option, the monitoring apparatus may also measure inhalation/exhalation cycles and/or strength and use this information in the estimation of a potential hypoxia situation.

The present invention is not solely limited to the above described embodiments but may be amended within the scope of the amended claims.

The invention claimed is:

1. A method for monitoring breathing air of a person breathing via a face mask, the method comprising:
   conducting a flow of fluid to be used as the breathing air through a fluid passage of a monitoring apparatus to a breathing hose of the face mask;
   measuring a pressure of the breathing air inside the fluid passage of the monitoring apparatus;
   measuring partial pressure of oxygen in the breathing air inside the fluid passage of the monitoring apparatus before the oxygen enters the breathing hose of the face mask;

estimating a partial pressure of oxygen in lungs of the person on the basis of the measured pressure of the breathing air and the measured partial pressure of oxygen in the breathing air;

comparing the estimated partial pressure of oxygen in the lungs with a pre-determined threshold partial pressure value and taking at least a partial pressure of water vapor of the lungs into account in the comparison; and providing an indication of impending hypoxia, if the comparison indicates that the estimated partial pressure of oxygen in the lungs is at a level lower than the threshold value.

2. The method according to claim 1, wherein the method further comprises at least one of the following:
providing the indication at least as a haptic indication;
providing the indication at least as a visual indication;
providing the indication at least as an audible indication.

3. The method according to claim 2, wherein the method further comprises:
providing the haptic indication by a vibrating element of the face mask.

4. The method according to claim 1, wherein the person is travelling in a cabin of an airplane, wherein the method further comprises:
measuring pressure of the cabin of the airplane; and
providing a warning to the person if the cabin is unpressurised.

5. The method according to claim 4, wherein the method further comprises:
measuring altitude of the airplane; and
using the measured altitude to determine whether to provide another warning to the person.

6. The method according to claim 1, wherein the method further comprises:
generating the breathing air by an onboard oxygen generation system.

7. The method according to claim 1, wherein the method further comprises:
measuring a concentration of one or more other gaseous compounds in the breathing air;
comparing the concentration to another threshold; and
generating an indication that the concentration of the one or more other gaseous compounds is above the another threshold.

8. The method according to claim 1, wherein the method further comprises:
examining whether the measured pressure of the breathing air inside the fluid passage changes; and
determining that there is leakage between the monitoring apparatus and the face mask if changes in the measured pressure of the breathing air are not detected.

9. The method according to claim 1, wherein the method further comprises measuring a respiration frequency of the person.

10. An apparatus for monitoring breathing air of a person breathing via a face mask, the apparatus comprising:
a fluid passage configured to conduct a flow of fluid to be used as the breathing air through the apparatus;
a conduit coupling the fluid passage of the apparatus with the face mask, wherein the conduit is configured to conduct the flow of fluid from the fluid passage to the face mask;
a pressure sensor for measuring a pressure of the breathing air in the fluid passage;
a partial pressure sensor for measuring a partial pressure of oxygen in the breathing air in the fluid passage before the oxygen enters the face mask; and
a processor;
wherein the processor is configured to:
estimate a partial pressure of oxygen in lungs of the person on the basis of the measured pressure of the breathing air and the measured partial pressure of oxygen; and
compare the estimated partial pressure of oxygen in the lungs with a threshold and take at least a partial pressure of water vapor of the lungs into account in the comparison;
wherein the apparatus further comprises a signal generation element configured to provide an indication of impending hypoxia to the person when the comparison indicates that the estimated partial pressure of oxygen in the lungs is at a level lower than the threshold.

11. The apparatus according to claim 10, wherein the apparatus is configured to:
provide the indication at least as a haptic indication;
provide the indication at least as a visual indication;
provide the indication at least as an audible indication.

12. The apparatus according to claim 10, wherein the fluid passage is configured to receive fluid to be inhaled and to output the fluid to the conduit coupling the fluid passage with the face mask.

13. The apparatus according to claim 12, wherein the apparatus further comprises a measurement chamber configured to accommodate the pressure sensor and the partial pressure sensor; and the measurement chamber has a flow connection with the fluid passage.

14. The apparatus according to claim 12, wherein the apparatus is configured to:
examine whether the measured pressure of the breathing air inside the fluid passage changes; and
determine that there is leakage between the monitoring apparatus and the face mask if changes in the measured pressure of the breathing air are not detected.

15. The apparatus according to claim 12, wherein the apparatus is configured to measure a respiration frequency of the person.

16. The apparatus according to claim 10, wherein the apparatus further comprises at least one of:
a cabin pressure sensor;
a temperature sensor;
an altimeter;
a voltage measurement sensor to measure a voltage level of a battery of the apparatus;
a circuitry configured to measure concentration of one or more other gaseous compounds.

* * * * *